United States Patent [19]
Cartwright et al.

[11] Patent Number: 6,034,010
[45] Date of Patent: Mar. 7, 2000

[54] MICROPOROUS FABRIC CONTAINING A MICROBIAL ADSORBENT

[75] Inventors: William Francis Cartwright; Carol Ann Blaney, both of Roswell, Ga.

[73] Assignee: Kimberly-Clark Worldwide, Inc., Neenah, Wis.

[21] Appl. No.: 08/936,156

[22] Filed: Sep. 24, 1997

Related U.S. Application Data

[63] Continuation of application No. 08/811,753, Mar. 6, 1997, abandoned, which is a continuation of application No. 08/470,508, Jun. 6, 1995, abandoned.

[51] Int. Cl.[7] ........................................ B32B 5/16
[52] U.S. Cl. ..................... 442/417; 442/181; 442/400; 442/401
[58] Field of Search ................... 442/181, 400, 442/401, 417

[56] References Cited

U.S. PATENT DOCUMENTS

| | | | |
|---|---|---|---|
| 3,276,944 | 10/1966 | Levy | 161/150 |
| 3,316,136 | 4/1967 | Pufahl | 156/160 |
| 3,338,992 | 8/1967 | Kinney | 264/24 |
| 3,341,394 | 9/1967 | Kinney | 161/72 |
| 3,502,538 | 3/1970 | Petersen | 161/150 |
| 3,502,763 | 3/1970 | Hartmann | 264/210 |
| 3,542,615 | 11/1970 | Dobo et al. | 156/181 |
| 3,676,242 | 7/1972 | Prentice | 156/62.4 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 3,909,009 | 9/1975 | Cvetko et al. | 274/37 |
| 3,935,363 | 1/1976 | Burkholder et al. | 428/281 |
| 3,949,128 | 4/1976 | Ostermeier | 428/152 |
| 3,973,063 | 8/1976 | Clayton | 428/35 |
| 4,041,203 | 8/1977 | Brock et al. | 428/157 |
| 4,042,740 | 8/1977 | Krueger | 428/138 |
| 4,081,301 | 3/1978 | Buell | 156/164 |
| 4,087,486 | 5/1978 | Fielding et al. | 260/897 |
| 4,100,324 | 7/1978 | Anderson et al. | 428/288 |
| 4,104,404 | 8/1978 | Bieler et al. | 428/35 |

(List continued on next page.)

FOREIGN PATENT DOCUMENTS

| | | |
|---|---|---|
| 803714 | 1/1969 | Canada . |
| 1255978 | 6/1989 | Canada . |
| 1272115 | 7/1990 | Canada . |
| 2025186 | 9/1990 | Canada . |
| 2028495 | 4/1991 | Canada . |
| 2032061 | 6/1991 | Canada . |
| 2033844 | 7/1991 | Canada . |
| 1305300 | 7/1992 | Canada . |
| 1312426 | 1/1993 | Canada . |
| 1317424 | 5/1993 | Canada . |

(List continued on next page.)

OTHER PUBLICATIONS

Database WPI, Week 8636, Derwent Publications Ltd., London, GB; AN 86–236752 & JP–A–61 167 550 (Toyo Chemical KK), Jul. 29, 1986, Abstract.
Database WPI, Week 8849, Derwent Publications Ltd., London, GB; AN 88–351188 & JP–A–63 264 336 (Asahi Chemical Ind KK), Nov. 1, 1988, Abstract.
Database WPI, Week 8120, Derwent Publications Ltd., London, GB; AN 81–35328d & JP–A–56 032 241 (Mitsui Toatsu Chem Inc.), Apr. 1, 1981, Abstract.

(List continued on next page.)

*Primary Examiner*—Christopher Raimund
*Attorney, Agent, or Firm*—James E. Ruland

[57] ABSTRACT

Disclosed is a fabric which includes a microbial adsorbent and which is capable of providing a microbial barrier while still being able to allow passage of water vapor. The fabric is formed from a plurality of fibers which define at least one microporous passageway which allows communication, through the fabric, between its respective first and second surfaces. In particular, a portion of the microporous passageway is defined by the microbial adsorbent so that microbes attempting to pass through the fabric via such a passageway must pass in close proximity to the microbial adsorbent. This arrangement allows the microbial adsorbent to interdict the microbe by adsorbing it. Passage of the microbe through the fabric is thereby prohibited. Laminates of the fabric with other materials are also disclosed.

30 Claims, 2 Drawing Sheets

U.S. PATENT DOCUMENTS

| | | | |
|---|---|---|---|
| 4,144,370 | 3/1979 | Boulton | 428/233 |
| 4,185,135 | 1/1980 | Huff | 428/96 |
| 4,254,175 | 3/1981 | Kubat et al. | 428/213 |
| 4,278,524 | 7/1981 | Kadija | 204/252 |
| 4,297,157 | 10/1981 | Van Vliet | 156/164 |
| 4,297,408 | 10/1981 | Stead et al. | 428/240 |
| 4,300,967 | 11/1981 | Sigl | 156/164 |
| 4,307,143 | 12/1981 | Meitner | 252/91 |
| 4,318,408 | 3/1982 | Korpman | 128/287 |
| 4,340,563 | 7/1982 | Appel et al. | 264/518 |
| 4,341,213 | 7/1982 | Cohen | 128/284 |
| 4,348,444 | 9/1982 | Craig | 428/137 |
| 4,379,192 | 4/1983 | Wahlquist et al. | 428/156 |
| 4,430,381 | 2/1984 | Harvey et al. | 428/284 |
| 4,434,258 | 2/1984 | Schumacher et al. | 524/13 |
| 4,443,513 | 4/1984 | Meitner et al. | 422/195 |
| 4,446,189 | 5/1984 | Romanek | 428/152 |
| 4,449,977 | 5/1984 | Korpman | 604/366 |
| 4,454,055 | 6/1984 | Richman et al. | 252/194 |
| 4,472,328 | 9/1984 | Sugimoto et al. | 264/41 |
| 4,500,670 | 2/1985 | McKinley et al. | 524/445 |
| 4,522,203 | 6/1985 | Mays | 128/132 D |
| 4,525,407 | 6/1985 | Ness | 428/138 |
| 4,568,341 | 2/1986 | Mitchell et al. | 604/368 |
| 4,579,729 | 4/1986 | Schoenthal et al. | 423/626 |
| 4,585,604 | 4/1986 | Okuyama et al. | 264/41 |
| 4,595,629 | 6/1986 | Mays | 428/286 |
| 4,606,964 | 8/1986 | Wideman | 428/152 |
| 4,606,970 | 8/1986 | Sharps, Jr. | 428/301 |
| 4,626,252 | 12/1986 | Nishizawa et al. | 604/370 |
| 4,650,481 | 3/1987 | O'Connor et al. | 604/380 |
| 4,656,062 | 4/1987 | Harriett | 427/397.8 |
| 4,657,802 | 4/1987 | Morman | 428/152 |
| 4,681,793 | 7/1987 | Linman et al. | 428/138 |
| 4,692,368 | 9/1987 | Taylor et al. | 428/137 |
| 4,704,238 | 11/1987 | Okuyama et al. | 264/41 |
| 4,707,398 | 11/1987 | Boggs | 428/224 |
| 4,720,415 | 1/1988 | Vander Wielen et al. | 428/152 |
| 4,721,511 | 1/1988 | Kupits | 8/188 |
| 4,725,473 | 2/1988 | Van Gompel et al. | 428/156 |
| 4,741,944 | 5/1988 | Jackson et al. | 428/152 |
| 4,748,978 | 6/1988 | Kamp | 128/156 |
| 4,758,617 | 7/1988 | Taniouku et al. | 524/413 |
| 4,761,324 | 8/1988 | Rautenberg et al. | 428/198 |
| 4,793,956 | 12/1988 | Nogiwa et al. | 264/41 |
| 4,814,124 | 3/1989 | Aoyama et al. | 264/41 |
| 4,822,350 | 4/1989 | Ito et al. | 604/372 |
| 4,826,516 | 5/1989 | Matsuoka et al. | 55/388 |
| 4,837,079 | 6/1989 | Quantrille et al. | 428/288 |
| 4,879,078 | 11/1989 | Antoon, Jr. | 264/41 |
| 4,883,549 | 11/1989 | Frost et al. | 156/161 |
| 4,902,544 | 2/1990 | Kim et al. | 428/36.1 |
| 4,921,653 | 5/1990 | Aoyama et al. | 264/41 |
| 4,929,303 | 5/1990 | Sheth | 156/209 |
| 4,935,267 | 6/1990 | Johnson et al. | 428/198 |
| 4,957,943 | 9/1990 | McAllister et al. | 521/64 |
| 4,981,747 | 1/1991 | Morman | 428/198 |
| 4,983,450 | 1/1991 | Yanagihara et al. | 428/283 |
| 5,011,698 | 4/1991 | Antoon, Jr. et al. | 426/395 |
| 5,051,189 | 9/1991 | Farrah | 210/679 |
| 5,069,907 | 12/1991 | Mixon et al. | 424/445 |
| 5,110,769 | 5/1992 | Welsh et al. | 501/12 |
| 5,114,781 | 5/1992 | Morman | 428/198 |
| 5,116,662 | 5/1992 | Morman | 428/198 |
| 5,143,679 | 9/1992 | Weber et al. | 264/288.8 |
| 5,169,712 | 12/1992 | Tapp | 428/315.5 |
| 5,174,231 | 12/1992 | White | 112/420 |
| 5,190,533 | 3/1993 | Blackburn | 604/367 |
| 5,208,098 | 5/1993 | Stover | 428/284 |
| 5,244,716 | 9/1993 | Thornton et al. | 428/198 |
| 5,261,899 | 11/1993 | Visscher et al. | 604/367 |
| 5,296,290 | 3/1994 | Brassington | 428/300 |
| 5,300,192 | 4/1994 | Hansen et al. | 162/184 |
| 5,328,758 | 7/1994 | Markell et al. | 428/281 |
| 5,336,552 | 8/1994 | Strack et al. | 428/224 |
| 5,352,216 | 10/1994 | Shiono et al. | 604/312 |
| 5,405,644 | 4/1995 | Ohsumi et al. | 427/2.31 |
| 5,409,761 | 4/1995 | Langley | 428/198 |

FOREIGN PATENT DOCUMENTS

| | | |
|---|---|---|
| 066672 | 12/1982 | European Pat. Off. . |
| 084903 | 8/1983 | European Pat. Off. . |
| 0 116 865 | 8/1984 | European Pat. Off. . |
| 192965 | 9/1986 | European Pat. Off. . |
| 0 297 538 | 1/1989 | European Pat. Off. . |
| 302597A2 | 2/1989 | European Pat. Off. . |
| 309073 | 3/1989 | European Pat. Off. . |
| 323629 | 7/1989 | European Pat. Off. . |
| 0 330 783 | 9/1989 | European Pat. Off. . |
| 360929 | 4/1990 | European Pat. Off. . |
| 403187 A1 | 8/1990 | European Pat. Off. . |
| 391661 | 10/1990 | European Pat. Off. . |
| 399439A3 | 11/1990 | European Pat. Off. . |
| 409567A2 | 1/1991 | European Pat. Off. . |
| 444671A3 | 2/1991 | European Pat. Off. . |
| 422561A3 | 4/1991 | European Pat. Off. . |
| 257280B1 | 9/1991 | European Pat. Off. . |
| 482918A3 | 4/1992 | European Pat. Off. . |
| 307116B1 | 8/1993 | European Pat. Off. . |
| 556749A1 | 8/1993 | European Pat. Off. . |
| 599425A1 | 6/1994 | European Pat. Off. . |
| 620111A1 | 10/1994 | European Pat. Off. . |
| 0 691 203 | 1/1996 | European Pat. Off. . |
| 2260716 | 5/1974 | Germany . |
| 43 11 422 | 10/1994 | Germany . |
| 62-282003 | 12/1987 | Japan . |
| 1-144431 | 6/1989 | Japan . |
| 2-36938 | 2/1990 | Japan . |
| 4-227260 | 8/1992 | Japan . |
| 793072 | 6/1979 | South Africa . |
| 1519172 | 7/1978 | United Kingdom . |
| 1575010 | 9/1980 | United Kingdom . |
| 2023493B | 10/1982 | United Kingdom . |
| 2115702A | 9/1983 | United Kingdom . |
| 2115853A | 12/1984 | United Kingdom . |
| 2272917A | 6/1994 | United Kingdom . |
| 2285408A | 7/1995 | United Kingdom . |
| 2290052A | 12/1995 | United Kingdom . |
| 87 01400 | 3/1987 | WIPO . |
| 88 01570 | 3/1988 | WIPO . |
| 90/06228 | 6/1990 | WIPO . |
| 91/02643 | 3/1991 | WIPO . |
| 91/11324 | 8/1991 | WIPO . |
| 93/11725 | 6/1993 | WIPO . |
| 93/11726 | 6/1993 | WIPO . |
| 93/21013 | 10/1993 | WIPO . |
| 93/22995 | 11/1993 | WIPO . |
| 94/09193 | 4/1994 | WIPO . |
| 94/20298 | 9/1994 | WIPO . |
| 95 10940 | 4/1995 | WIPO . |
| 95/16562 | 6/1995 | WIPO . |

OTHER PUBLICATIONS

Database WPI, Week 8621, Derwent Publications Ltd., London, GB: AN 86–135042/21 & JP–A–61 072 543 (Komatsu Seiren KK), Apr. 14, 1986, Abstract.

"Specialty Clay Product Summary," Technical Data Sheet, VOLCLAY MPS 1, IC–590, May 1992, American Colloid Company.

Database WPI, Section Ch. Week 9517, Derwent Publications Ltd., London, GB; Class A60, AN 95–128842 XP002014413 & JP,A,07 054 208 (Teijin Ltd.), Feb. 28, 1995, See Abstract.

Database WPI, Section Ch, Week 9412, Derwent Publications Ltd., London, GB; Class A32, AN 94–097914 XP002014436 & JP,A,06 049 253, Feb. 22, 1994, See Abstract.

Database WPI, Section Ch, Week 9247, Derwent Publications Ltd., London, GB; Class A32, AN 92–385722 XP002014437 & JP,A,04 284 235, Oct. 8, 1992, See Abstract.

Database WPI, Section Ch, Week 9145, Derwent Publications Ltd., London, GB; Class A94, AN 91–329942 XP002014438 & JP,A,03 221 540, Sep. 30, 1991, See Abstract.

*The United States Pharmacopeia USP XXII—The National Formulary NF XVII*, Jan. 1, 1990, p. 1902.

*Kirk–Othmer Encyclopedia of Chemical Technology*, 3rd ed., vol. 6, pp. 207–209, John Wiley & Sons, NY, Mar. 1979.

*The Condensed Chemical Dictionary*, 10th ed., Gessner G. Hawley, Van Nostrand Reinhold Co., NY, Jan. 1981, p. 115.

"Effects of Bentonite Clay Solids on Poliovirus Concentration from Water by Microporous Filter Methods," *Applied and Environmental Microbiology*, Apr. 1985, pp. 795–798.

Farrah & Erdos, Jan. 1991, "The production of antibacterial tubing, sutures, and bandages by in situ precipitation of metallic salts," Dept. of Microbiology & Cell Science, U. of Florida, pp. 445–449.

"Inactivation of Bacteria by Solids Coated with Magnesium Peroxide," Asghari & Farrah, *Journal of Environmental Science and Health*, Jan. 1993, pp. 779–793.

"Specialty Clay Product Summary," Technical Data Sheet, VOLCLAY MPS 1, IC–590, May 1992, American Colloid Company.

MICROPOROUS FABRIC CONTAINING A MICROBIAL ADSORBENT

This application is a continuation of application Ser. No. 08/811,753 entitled "Microporous Fabric Containing a Microbial Adsorbent" and filed in the U.S. Patent and Trademark Office on Mar. 6, 1997, abandoned, which is a continuation of application Ser. No. 08/470,508 entitled "Microporous Fabric Containing a Microbial Adsorbent" and filed in the U.S. Patent and Trademark Office on Jun. 6, 1995 abandoned. The entirety of this application is hereby incorporated by reference.

FIELD OF THE INVENTION

The field of the present invention encompasses fabrics which possess antimicrobial characteristics.

BACKGROUND OF THE INVENTION

Films have been traditionally used to provide barrier properties in single-use items including, but not limited to, articles of clothing in general, protective apparel, health care related products including surgical drapes, gowns, and sterile wrap and personal care absorbent products such as diapers, training pants, incontinence garments, sanitary napkins, bandages, and the like. In personal care absorbent products such as infant diapers and adult incontinence products, films are used as the outer covers with the purpose of preventing body wastes from contaminating the clothing, bedding, and other aspects of the surrounding environment of use. In the area of protective apparel including hospital gowns and other clean room garments, films are used to prevent exchange of microorganisms between the wearer and the patient. These films are usually one to two mils in thickness and have a basis weight of approximately 0.7 to 1.5 ounces per square yard. Polyolefin films are most commonly used in such areas.

One of the significant disadvantages in the utilization of films as barrier materials in most, if not all, of these types of products is that the films do their job too well. That is, they form a complete barrier. Complete barriers of this type create an entirely new problem in that they block the egress of water vapor from the person or item which the film enwraps. Accordingly, those wearing garments formed from such materials tend to rapidly become quite uncomfortable due to a build-up of water vapor which is given off by the individual but not allowed to pass through the film. The water vapor remains between the individual and the garment or item made from the material. The individual rapidly develops a feeling of being "sweaty" or "sticky" as the relative humidity in that confined area builds up and water vapor condenses therein.

In response to this problem, those of skill in the art have attempted to manufacture protective garments and other items where passage of microbes is undesirable from materials which allow the passage of water vapor. Such materials include, for example, nonwoven webs and laminates thereof as discussed in detail in U.S. Pat. No. 4,041,203 to Brock et al. This patent is hereby incorporated herein by reference in its entirety.

Microporous varieties of films, either by themselves or incorporated in laminates, have also been used in such products in an attempt to provide articles with more garment-like attributes, such as the ability to reduce the relative humidity underneath the garment, thus maintaining a higher degree of comfort for the wearer.

However, the use of nonwoven webs and/or microporous films in certain protective apparel has not been without difficulties. For example, utilization of such materials has generated concerns about their ability to prevent transfer of microorganisms because the size of microorganisms such as viruses and bacteria are typically much smaller than the pores of microporous films. Nonwoven web materials, typically, also are characterized by passageways therethrough which, while they may retard the progress of microbes, do not guarantee complete barrier properties with respect to them. For these reasons, neither of these arrangements has proven to be completely satisfactory in view of the fact that they do not form a complete barrier for microbes.

Therefore, there remains a distinct need for a material which allows the passage of water vapor therethrough while effectively forming a barrier to the passage of small pathogens such as viruses, bacteria, cysts and nematodes. If such a material were a fabric such as a spunbonded or meltblown nonwoven web, it could be used alone or as one layer of a laminate to provide an overall material which would have effective microbial barrier properties, breathability (that is, allow passage of an adequate amount of water vapor) and tactile feel.

OBJECTS OF THE INVENTION

Accordingly, it is an object of the present invention to provide a fabric which allows the passage of water vapor while still being an effective barrier material for microbes such as viruses, bacteria, cysts, and nematodes.

It is a further object of the present invention to provide a fabric which also allows the passage of water vapor, is an effective barrier for microbes such as viruses, bacteria, cysts, and nematodes and, upon being exposed to a generally aqueous liquid, forms a physical barrier to the passage of such liquid therethrough in the area limited to such exposure.

It is yet another object of the present invention to provide a laminate of such a fabric with one or more other materials.

These and other objects and the broad scope of applicability of the present invention, will become apparent to those of skill in the art from the details given hereinafter. However, it should be understood that the detailed description of the presently preferred embodiments of the present invention is given only by way of illustration because various changes and modifications well within the spirit and scope of the invention will become apparent to those of skill in the art in view of this detailed description.

SUMMARY OF THE INVENTION

In response to the aforementioned difficulties encountered by those of skill in the art, we have invented a fabric having first and second surfaces and which includes a microbial adsorbent and which is capable of providing a microbial barrier while still being able to allow passage of water vapor. The fabric may be woven or nonwoven. For example, if the fabric is a nonwoven web it may be a spunbonded web or a meltblown web. The fabric is formed from a plurality of fibers. The fibers will be woven or, if the fabric is a nonwoven, interlaid in such a manner that the passageways through the fabric defined by the fibers form micropores. Accordingly, the fabric of the present invention will, in its broadest aspect, have a plurality of fibers which define at least one microporous passageway allowing communication, through the fabric, between the first and second surfaces. Such communication, in some embodiments, allows the passage of water vapor through the fabric. In particular, a portion of the microporous passageway is defined by a microbial adsorbent so that microbes attempting to pass through the fabric via a passageway must pass in close proximity to the microbial adsorbent. This arrangement allows the microbial adsorbent to interdict the microbe by adsorbing it and prohibiting its passage through the fabric.

In some embodiments the fabric may be formed from a thermoplastic polymer. For example, the thermoplastic polymer may be selected from the group including polyolefins, polyamides, polyesters and copolymers and blends in any combination of these and/or any other suitable material. For example, the polyolefin may be selected from the group consisting of polypropylenes, polyethylenes, polybutylenes and copolymers and blends thereof. The polyethylene may be linear low density polyethylene.

By specifically tailoring the type of microbial adsorbent present in the fabric, the fabric may be adapted to adsorb viruses, bacteria, cysts, or nematodes or any or all of these. Naturally the fabric may be adapted to adsorb specific types of viruses, bacteria, cysts, nematodes etc., depending upon the use to which it is to be assigned.

In certain embodiments, the fabric may be designed to not only act as a filter for microbes as a result of the presence of the microbial adsorbent but may also be designed to act as a physical (mechanical) barrier to liquids attempting to pass therethrough. To this end, the microbial adsorbent utilized may be one which, in the presence of a generally aqueous liquid, increases its volume at least 1.5 times in no more than 120 seconds. For example, the microbial adsorbent may be one which, in the presence of a generally aqueous liquid, increases its volume at least 1.5 times in no more than 60 seconds. More particularly, the microbial adsorbent may be one which, in the presence of a generally aqueous liquid, increases its volume at least 1.5 times in no more than 15 seconds. Even more particularly, the microbial adsorbent may be one which, in the presence of a generally aqueous liquid, increases its volume at least 2 times in no more than 1 second. In the event such a microbial adsorbent is utilized, the adsorbent will, upon being contacted with the generally aqueous liquid, increase in size and swell. The swelling serves to block the microporous passageway with which the microbial adsorbent is in close proximity. Blockage of the passageway creates a physical barrier within the microporous passageway with the consequence that no further liquid can pass.

An alternative manner by which physical blockage may be obtained, if the microbial adsorbent which is desired to be utilized does not have the capability of swelling (increasing its size), is that the fabric may also include a loading of another particulate material which, itself, swells in the presence of a generally aqueous liquid. In some embodiments, particulates of the swellable material and the microbial adsorbent may be incorporated into the fabric in an agglomerated fashion so that each individual agglomerate contains some of the non-swellable microbial adsorbent and some of the swellable material. Of course, the particles of microbial adsorbent and swellable material must be located along the microporous passageways which transit the fabric. Otherwise, the particles could not perform their intended function.

In any of these embodiments the swellable material is one which can increase its volume at least 1.5 times in no more than 120 seconds in the presence of a generally aqueous liquid. For example, the swellable material may be one which, in the presence of a generally aqueous liquid, increases its volume at least 1.5 times in no more than 60 seconds. More particularly, the swellable material may be one which, in the presence of a generally aqueous liquid, increases its volume at least 1.5 times in no more than 15 seconds. Even more particularly, the swellable material may be one which, in the presence of a generally aqueous liquid, increases its volume at least 2 times in no more than 1 second.

The microbial adsorbent may be any such adsorbent which is compatible with the fabric material being utilized. In some embodiments the microbial adsorbent may be a derivitized silane such as, for example, 3-(trimethoxysilyl) propyldimethyloctadecyl ammonium chloride. [$(CH_3)_3Si(CH_2)_3N^+ (CH_3)_2C_{18}H_{37}Cl^-$] This material was formerly available from Dow Corning under the trade designation Dow Corning 5700. It now is available from Aegis Environmental. In other embodiments the microbial adsorbent is a heavy metal. For example, the heavy metal may be silver.

In other embodiments the microbial adsorbent may be a metallic salt. For example, the metallic salt may be a water-insoluble polyvalent metal salt. The water-insoluble polyvalent metal salt may be a salt of a metal selected from the group including Group IB, Group IIA, Group IIB, Group IIIA, Group IVB, Group VIB metals. More particularly, the metal may be selected from the group including iron, aluminum, lead, magnesium, silver, calcium and alloys of one or more of iron, aluminum, lead, magnesium, silver and calcium. The salt may be selected from the group including hydroxides, phosphates, chromates, oxides and peroxides. For example, the salt may be selected from the group including one or more of ferric hydroxides, ferrous hydroxides, aluminum hydroxides, magnesium hydroxide, magnesium oxide, magnesium peroxide, lead chromate and calcium hydroxide.

In some embodiments the microbial adsorbent may be selected from the group including colloidal clays. For example, the colloidal clay may be a bentonite such as sodium bentonite and/or calcium bentonite. The colloidal clay may, in some embodiments, be hectorite.

The microbial filter fabric of the present invention may be advantageously formed into a wide variety of items where it is desired to have a material which allows passage of, for example, water vapor but which prohibits the passage of microbes therethrough. For example, the item may be a garment. such as a surgical gown, foot protectors, face masks, head or hair coverings, aprons, jackets, pants gloves, coveralls and, generally speaking, all clean room attire.

Alternatively it may be incorporated into a product such as, for example, a sterile wrap material which is used to maintain the sterile field around a doctor's tools until they are utilized in an operation.

Likewise, the fabric of the present invention may conveniently be formed into a surgical drape for use on a patient during an operation.

DEFINITIONS

As used herein the term "breathable" refers to any material which has a water vapor transmission rate (WVTR) of at least 300 grams per square meter per 24 hours when measured in accordance with ASTM E 96–80.

As used herein the term "microbial adsorbent" refers to any material which has the ability to hold and/or inactivate microbes such as, for example, viruses, bacteria, cysts and/or nematodes on or near its surface.

As used herein the term "microporous passageway" refers to any passageway which, at some point along its length, has a diameter of fifty (50) microns or less.

As used herein the term "microporous fabric refers to a fabric having a plurality of microporous passageways therethrough to make the fabric breathable. The microporous fabric will also have a hydrohead of at least 25 centimeters of water when its hydrohead is measured in accordance with Method 5514—Federal Test Methods Standard No. 191A. For example, the microporous fabric may have a hydrohead of at least 50 centimeters of water when so measured.

As used herein the term "generally aqueous liquid" refers to any liquid which has, as a major component, water. All bodily fluids including, without limitation, blood, saliva, menses, mucus, lymph fluid and urine, are expressly included within this definition.

Whether a material is "swellable" is determined by first providing 100 mL of water contained in a glass-stoppered cylinder of 100 mL capacity. Next a first two (2) gram portion of the material is dropped onto the surface of the water and allowed to completely settle. Then, a second two (2) gram portion of the material being tested is dropped onto the surface. After two (2) hours, the volume occupied by the material at the bottom of the cylinder is observed. For a material to be "swellable", the material at the bottom of the cylinder must have an apparent volume of not less than 6 mL.

As used herein the term "fabric" is intended to encompass any sheet-like material which is formed, in whole or part, from a plurality of fibers. A fabric may be woven or nonwoven. Typical examples of nonwoven fabrics are meltblown webs and spunbonded webs.

As used herein, the term "nonwoven web" refers to a web that has a structure of individual fibers or filaments which are interlaid, but not in an identifiable repeating manner.

As used herein the term "spunbond or spunbonded fibers" refers to fibers which are formed by extruding molten thermoplastic material as filaments from a plurality of fine, usually circular capillaries of a spinnerette with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. Nos. 3,502,763 and 3,909,009 to Levy, and U.S. Pat. No. 3,542,615 to Dobo et al. which are all herein incorporated by reference.

As used herein the term "meltblown fibers" means fibers formed by extruding a molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers. Meltblowing is described, for example, in U.S. Pat. No. 3,849,241 to Buntin, U.S. Pat. No. 4,307,143 to Meitner et al., and U.S. Pat. No. 4,707,398 to Wisneski et al. which are all herein incorporated by reference.

DETAILED DESCRIPTION OF THE INVENTION

Figure 1:
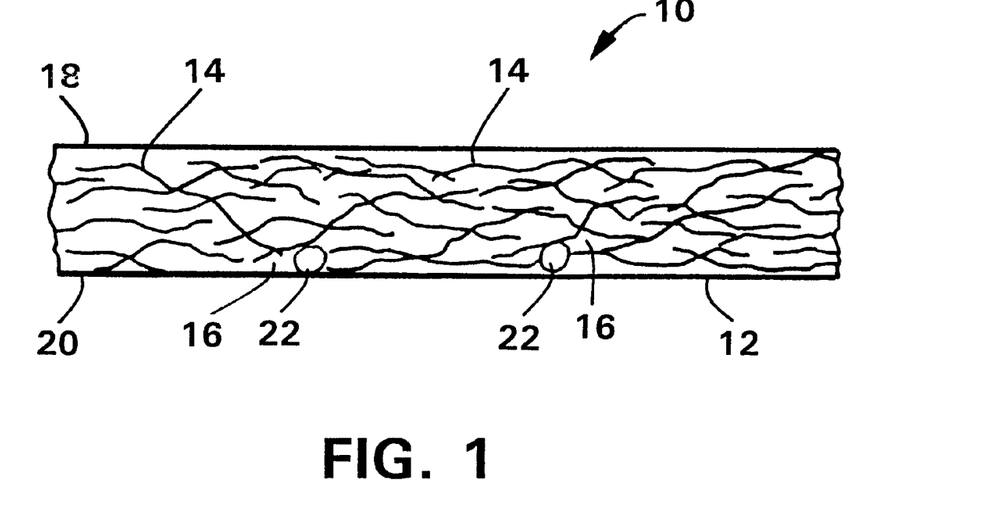
FIG. 1 is a schematic, highly enlarged cross-sectional view of a breathable, microbial barrier fabric designed in accordance with the teachings of the present invention.

Turning now to the drawings where like reference numerals represent like or equivalent structures or process steps, an improved microporous fabric 10 of the present invention is depicted. Typically, the fabric 10 will be formed from a nonwoven web 12 of a thermoplastic material. Of course, the fabric 10 may be formed, in other embodiments, from a wide variety of woven materials. The nonwoven web 12 will be formed from a plurality of fibers 14. The random intertwining of the fibers 14 of the nonwoven web 12 form tortuous passageways 16 from a first surface 18 of the fabric 10 to a second surface 20 of the fabric 10. That is to say, the fibers 14 of the web 12, in combination, form a multitude of passageways trough the fabric 10 as is conventionally known. For purposes of the present invention, the fibers 14 should be laid down in such a fashion as to assure that the passageways 16 through the web 12 are microporous passageways 16. While low denier meltblown fibers are well suited for this task, any type of fiber which can be arranged to assure that the passageways 16 through the fabric 10 are microporous will suffice. Those of ordinary skill in the art will readily recognize that typical microporous fabrics 10 possess a multitude of such passageways 16 per square inch. The fabric 10 is configured so that a particle 22 of a material which is a microbial adsorbent is positioned at some point along the length of the passageway 16 between the first surface 18 of the fabric 10 and the second surface 20 of the fabric 10. In most instances, the lay-down of the fibers 14 will be controlled so that the passageways 16 will be sized in such a manner as to allow the passage of water vapor through the fabric 10. That is, the fabric 10 is breathable. In particular, a portion of the microporous passageway 16 is defined by the microbial adsorbent 22 so that microbes (not illustrated) attempting to pass through the fabric 10 via a passageway 16 must pass in close proximity to the microbial adsorbent 22. This arrangement allows the microbial adsorbent 22 to interdict microbes by adsorbing them and prohibiting their passage through the fabric 10 while still retaining the breathability of the fabric 10.

In some embodiments the thermoplastic material 12 may be selected from the group including polyolefins, polyamides, polyesters and copolymers and blends in any combination of these and/or any other suitable material. For example, the polyolefin may be selected from the group consisting of polypropylenes, polyethylenes, polybutylenes and copolymers and blends thereof. The polyethylene may be linear low density polyethylene.

By specifically tailoring the type of microbial adsorbent 22 present in the fabric 10, the fabric 10 may be adapted to adsorb a wide variety of pathogens. For example, the fabric 10 may be tailored to act as a filter for viruses, bacteria, cysts, and/or nematodes. Naturally the fabric 10 may be adapted to adsorb specific types of viruses, bacteria, cysts, and/or nematodes depending upon the use to which it is to be assigned. Utilization of a pathogen-specific adsorbent readily accomplishes this result.

In certain embodiments, the fabric 10 may be designed to not only act as a filter (adsorbent) for microbes as a result of the presence of the microbial adsorbent 22 but may also be designed to act as a physical (mechanical) barrier to liquids attempting to pass therethrough. To this end, the microbial adsorbent 22 utilized may be a swellable one which, in the presence of a generally aqueous liquid, can increase its volume at least 1.5 times in no more than 120 seconds. For example, the microbial adsorbent 22 may be one which, in the presence of a generally aqueous liquid, increases its volume at least 1.5 times in no more than 60 seconds. More particularly, the microbial adsorbent 22 may be one which, in the presence of a generally aqueous liquid, increases its volume at least 1.5 times in no more than 15 seconds. Even more particularly, the microbial adsorbent 22 may be one which, in the presence of a generally aqueous liquid, increases its volume at least 2 times in no more than 1 second. In the event such a microbial adsorbent 22 is utilized, the adsorbent 22 will, upon being contacted with the generally aqueous liquid, increase in size and swell. The swelling serves to block the microporous passageway 16 which is in close proximity to the swellable adsorbent 22. Blockage of the passageway 16 creates a physical barrier within the microporous passageway 16 with the consequence that no liquid can pass therethrough. Thus, a physical or mechanical barrier (dam) is formed in the passageway 16 which closes off the passageway 16. The net result of this embodiment is that the fabric 10 is "intelligent" in that it breathes and allows water vapor to pass as long as the fabric 10 has not received a liquid insult. The microbial adsorbent 22 within the fabric 10 constantly interdicts pathogens such as viruses and bacteria so that they cannot pass through the fabric even though it is capable of allowing passage of water vapor. however, upon receipt of a liquid insult, the fabric self seals itself only in the area of the insult in order to prevent passage of the liquid therethrough. Throughout all of this the fabric 10 remains breathable because of the presence of numerous other micropores 16 which have not been blocked. A specific example of a swellable microbial adsorbent 22 is bentonite and, in particular, sodium bentonite.

Figure 2:
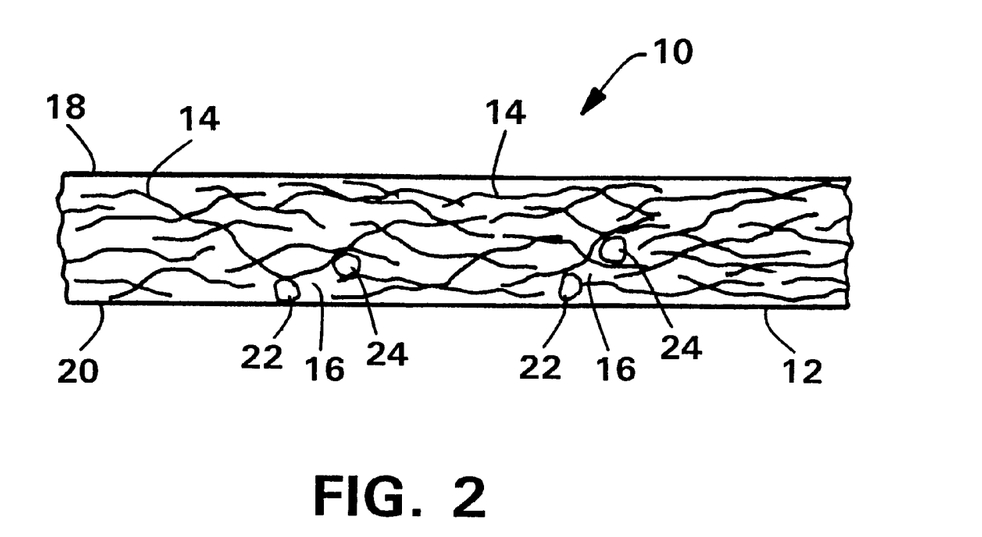
FIG. 2 is a schematic, highly enlarged cross-sectional view of an embodiment of a breathable, microbial barrier fabric designed in accordance with the teachings of the present invention and where the fabric also forms a physical barrier to the passage of liquids at the site of contact of the fabric by such a liquid.

FIG. 2 illustrates an alternative manner by which physical blockage of the passageway 16 may be obtained, if the microbial adsorbent 22 which is desired to be utilized does not have the capability of swelling (increasing its size), which is that the fabric 10 may also include a loading of another particulate material 24 which, itself, swells in the presence of a generally aqueous liquid. In some embodiments, particulates of the swellable material 24 and the microbial adsorbent 22 may be incorporated into the fabric 10 in an agglomerated fashion so that each individual particle contains some of the non-swellable microbial adsorbent 22 and some of the swellable material 24. In any of these embodiments the swellable material 24 is one which can increase its volume at least 1.5 times in no more than 120 seconds. For example, the swellable material 24 may be one which, in the presence of a generally aqueous liquid, increases its volume at least 1.5 times in no more than 60 seconds. More particularly, the swellable material 24 may be one which, in the presence of a generally aqueous liquid, increases its volume at least 1.5 times in no more than 15 seconds. Even more particularly, the swellable material 24 may be one which, in the presence of a generally aqueous liquid, increases its volume at least 2 times in no more than 1 second. Specific examples of such swellable materials 24 which may be utilized in conjunction with a non-swelling microbial adsorbent 22 include, without limitation, kaolins and diatomaceous earth. The diatomaceous earth may be treated, as is known to those in the art, so as to be positively charged. One constraint in this design is that the microbial adsorbent 22 and the swellable material 24 must both be exposed to the passageway 16 for each to perform their respective functions.

The microbial adsorbent 22 may be any such adsorbent 22 which is compatible with the fiber-forming material being utilized. In some embodiments the microbial adsorbent 22 is a heavy metal. For example, the heavy metal may be silver.

In other embodiments the microbial adsorbent 22 may be a metallic salt. For example, the metallic salt may be a water-insoluble polyvalent metal salt. The water-insoluble polyvalent metal salt may be a salt of a metal selected from the group including Group IB, Group IIA, Group IIB, Group IIIA, Group IVB, Group VIB metals. More particularly, the metal may be selected from the group including iron, aluminum, lead, magnesium, silver, calcium and alloys of one or more of iron, aluminum, lead, magnesium, silver and calcium. The salt may be selected from the group including hydroxides, phosphates, chromates, oxides and peroxides. For example, the salt may be selected from the group including one or more of ferric hydroxides, ferrous hydroxides, aluminum hydroxides, magnesium hydroxide, magnesium oxide, magnesium peroxide, lead chromate and calcium hydroxide.

In some embodiments the microbial adsorbent 22 may be selected from the group including colloidal clays. For example, the colloidal clay may be a bentonite such as sodium bentonite and/or calcium bentonite. In some embodiments the colloidal clay may be a hectorite.

The microbial filter fabric 10 of the present invention may be advantageously formed into a wide variety of items where it is desired to have a material which allows passage of, for example, water vapor but which prohibits the passage of microbes therethrough. For example, the item may be a garment such as a surgical gown, foot protectors, face masks, head or hair coverings, aprons, jackets, pants gloves, coveralls and, generally speaking, all clean room attire.

Alternatively the fabric 10 may be incorporated into a product such as, for example, a sterile wrap material which is used to maintain the sterile field around a doctor's tools until they are utilized in an operation.

Likewise, the fabric 10 of the present invention may conveniently be formed or incorporated into a surgical drape for use on a patient during an operation.

The fabric 10 of the present invention may be made by a wide variety of methods known to those of skill in the art. One method of forming the film 10 is described in detail in U.S. Pat. No. 4,100,324 entitled "Nonwoven Fabric And Method Of Producing Same" and issued on Jul. 11, 1978 in the names of Richard A. Anderson, Robert C. Sokolowski and Kurt W. Ostermeier. This application is hereby specifically incorporated by reference into the present application in its entirety. Fabrics 10 of the present invention can be formed using this process merely by substituting microbial adsorbent particles 22 as the additive to the fiber-forming stream. All other process steps remain essentially the same. of course, the microbial adsorbent 22 selected desirably will not chemically interfere with or adversely affect the extruded fibers 14 and will have the ability to be relatively uniformly dispersed throughout the fibers 14 upon their formation.

Alternatively, the microbial adsorbent 22 particles can be added to the thermoplastic material prior to its extrusion through the die tip to form the fibers. In this embodiment, it is necessary for the moisture content of the microbial adsorbent 22 to be maintained at 1%, by weight, or less for satisfactory extrusion to occur. Generally speaking, these microbial adsorbent 22 particles which are extruded will have an average particle size in the range of from about 0.1 to about 7 microns. Of course, the maximum particle size will be governed by the ultimate diameter of the fibers 14 which are to be formed. Typically the fabric 10 will contain at least about 30%, by weight of the fabric, of the adsorbent 22.

Figure 3:
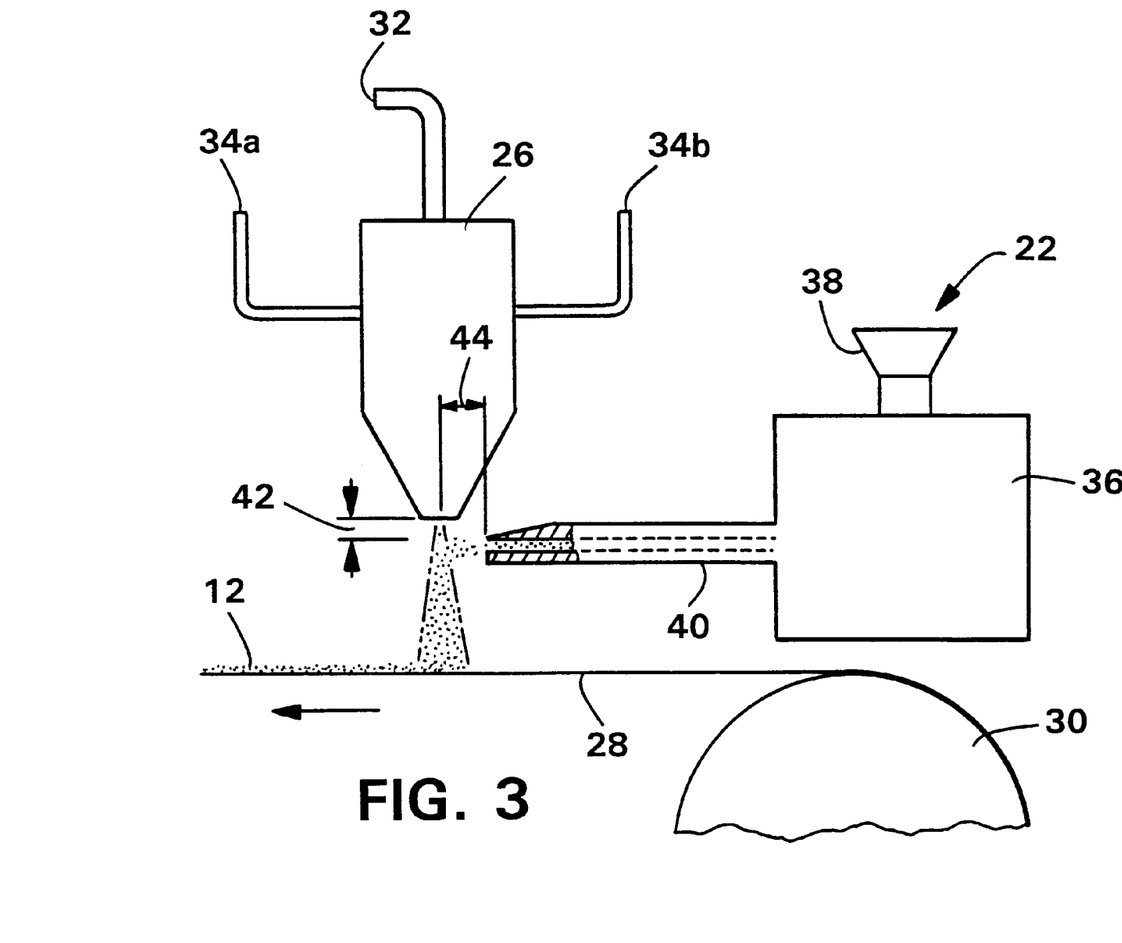
FIG. 3 is a schematic representation of a process for forming a microbial barrier fabric in accordance with the teachings of the present invention.

FIG. 3 schematically illustrates, in more detail, a process for forming a fabric 10 in accordance with the teachings of the present invention. This process is more completely described in U.S. Pat. No. 4,663,220. the entirety of this patent is hereby incorporated by reference herein. The fabric 10, in this embodiment, is formed from a meltblown nonwoven web 12 which may include substantially continuous microfibers 14. Alternatively, the microfibers 14 may be discontinuous, as is well known to those of skill in the art. Whether the fibers 14 are continuous or discontinuous depends on a variety of process variables which include, for example, the velocity of the attenuating gas, the temperature of the attenuating gas and the volume of attenuating gas passing through the air passageways in a given time period. The meltblown fibers 14 are formed by a conventional meltblowing die 26 and deposited on the surface of a foraminous belt 28. Other foraminous arrangements such as a drum arrangement may be utilized. One or more vacuum boxes (not shown) typically are located below the surface of the foraminous belt 28 and between a pair of rollers 30 one of which is shown in FIG. 3. The meltblowing die 26 is supplied with a thermoplastic material, which is to be formed into the fibers 14 from a conventional extruder arrangement (not shown), through an orifice 32. As is well known by those in the art, the meltblowing die 26 is also provided with pressurized air at orifices 34a and 34b. Thereafter, the microfibers 14 are expelled from the meltblowing die 26 and are collected as a fibrous nonwoven microporous web 12 on the surface of the belt 28 which is moving as indicated by the arrow. The vacuum boxes assist in retention of the microfibers 14 on the surface of the belt 28. Typically the tip of the meltblowing die 26 is from about 4 inches to about 24 inches from the surface of the foraminous endless belt 28 upon which the microfibers 14 are collected. The thus-collected, entangled microfibers 14 form a coherent, i.e. cohesive, fibrous microporous nonwoven web 12 which may be removed from the foraminous endless belt 28 by a pair of pinch rollers (not shown) which may be designed to press the entangled fibers 14 of the web 12 together to improve the integrity of the web 12. Thereafter, the web 12 may be transported by a conventional arrangement to a wind-up roll (not shown) for storage. Alternatively, the web 12 may be removed directly from the belt 28 by the wind-up roller. In some embodiments, the web 12 may be pattern-embossed as by ultrasonic embossing equipment (not shown) or other embossing equipment, such as, for example, the pressure nip formed between a heated calender and anvil roll (not shown).

FIG. 3 illustrates that the discrete particles of the microbial adsorbent are incorporated into the stream of meltblown fibers 14 after the expulsion of the fibers 14 from the meltblowing die 26 but prior to the deposition of the fibers 14 onto the belt 28. If the microbial adsorbent 22 is one which does not swell and it is desired that the fabric 10 which is being made to have the ability to form a mechanical barrier to liquid insults, additional particulates of fibrous materials which have the ability to swell may be conveniently added to the fiber stream at this point in the process. For example, it may be desirable to incorporate one or more types of swellable materials such a fibrous or particulate superabsorbent materials or wood pulp fibers or particulates into the fibers 14. Blends of two or more of such fibers or particulates can be so incorporated. This type of apparatus is conventionally referenced by those of skill in the art as "coforming" apparatus. Coforming generally refers to the process of adding fibers and/or particulates to the stream of newly formed fibers 14 prior to their deposition on the belt 28 and their subsequent formation into a nonwoven web 12.

FIG. 3 illustrates that, after formation of the microfibers 14, a stream of particulates of a microbial adsorbent 22 is generally uniformly injected into the stream of microfibers 14. As has been previously, stated, in some embodiments the microbial adsorbent 22 may be in the form of a fiber as opposed to particulate form. Distribution of the particulates of the microbial adsorbent 22 generally uniformly throughout the stream of microfibers 14 is preferably accomplished by merging a secondary gas stream (not shown) containing the particulates of microbial adsorbent 22 with the stream of microfibers 14. Apparatus for accomplishing this merger includes a conventional particulate injection system 36 which receives the particulates 22 in a hopper 38. The particulate injection system 36 conveys the particulates 22 toward the meltblown stream of fibers 14 through a forming duct or nozzle 40. The particulates 22 are conveyed through the nozzle 40 by means of the secondary stream of pressurized air.

The height 42 of the forming duct or nozzle 40 with respect to the tip of the die 26 may be adjusted to vary the properties of the coformed product. The height 42 and distance 44 values will also vary with the particular microbial adsorbent 22 being added to the microfibers 14. The width of the forming duct or nozzle 40 and the length that the forming duct or nozzle 82 extends from the particulate injection system 36 will have to be adjusted in order to obtain optimum distribution of the particulates 22 throughout the stream of meltblown microfibers 14. Preferably, the length of the forming duct or nozzle 40 should be as short as equipment design will allow.

FIG. 3 further illustrates that the gas stream carrying the particulates 22 is desirably moving in a direction which is generally perpendicular to the direction of movement of the stream of the microfibers 14 at the point of merger of the two gas streams. Other angles of merger of the two streams may be utilized. The velocity of the gas stream carrying the particulates 22 is usually adjusted so that it is less than the velocity of the gas stream which attenuates the microfibers 14. This allows the streams, upon merger and integration thereof, to flow in substantially the same direction as that of the stream of microfibers 14. Indeed, the merger of the two streams is preferably accomplished in a manner which is somewhat like an aspirating effect whereby the stream of particulates 22 is drawn into the stream of microfibers 14. It is also preferred that the velocity difference between the two gas streams be such that the particulates 22 are integrated into the microfibers 14 in a turbulent manner so that the particulates become thoroughly mixed with the microfibers 14. In general, increasing the velocity differential between the two streams produces a more homogeneous integration of the particulates 22 into the microfibers 14, and decreases in the velocity differential between the two streams are generally expected to produce concentrated areas of particulates 22 within the microfibers 14. Generally, for increased production rates it is desired for the gas stream which entrains and attenuates the stream of microfibers 14 to have an initial high velocity, for example from about 200 feet to about 1,000 feet per second and for the stream of gas which carries the particulates 22 to have an initial low velocity, for example from about 50 to about 200 feet per second. Of course, after the stream of gas that entrains and attenuates the extruded thermoplastic material into microfibers 14 exits the meltblowing die 26 it immediately expands and decreases in velocity.

Upon merging and integration of the stream of microbial adsorbent particulates 22 into the stream of microfibers 14 to generally uniformly distribute the particulates 22 throughout the stream of meltblown fibers 14, as discussed above, a composite stream of microfibers 14 and particulates 22 is formed. The microfibers 14 may still be semi-molten and tacky at the time of incorporation of the particulates 22 into the microfibers 14, and, in such a situation, the particulates 22 are not only mechanically entangled within the microfibers 14 but also usually become thermally bonded to the microfibers 14. However, if the microfibers 14 are not semi-molten and tacky at the time of incorporation of the particulates 22 therein, the particulates 22 will only be mechanically entangled within the microfibers 14.

In order to convert the composite stream of microfibers 14 and particulates 22 into a microporous fibrous nonwoven web 12 of microfibers 14 having the particulates 22 generally uniformly distributed throughout and, if desired, bonded to the microfibers 14 of the web 12, a collecting device is located in the path of the composite stream. The collecting device may be the foraminous rotating belt 28 illustrated in FIG. 3. A conventional vacuum arrangement (not shown) assists in retaining the composite mixture of fibers 14 and particulates 22 on the external surface of the belt 28. Other collecting devices are well-known to those of skill in the art and may be utilized in place of the rotating belt 28. For example, a porous rotating drum arrangement could be utilized. Thereafter, the web 12 may be removed from the belt 28 by a pair of nip rollers (now shown) and stored on a conventional wind-up roller, as previously discussed.

Those of skill in the art will readily recognize that numerous variations of this process are possible. For example, instead of utilizing conventional coforming apparatus, the particulates or fibers of microbial adsorbent may be extruded directly through the die 26. In this embodiment the particulates 22 would be incorporated directly into the fibers 14. In some of these embodiments the resulting fabric would include one or more fibers 14 having an outer surface. In some embodiments the fibers 14 will define at least one microporous passageway 16 allowing communication, through the fiber 14, between a first portion of the outer surface and a second portion of the outer surface of the fiber 14. As with the prior embodiments, a portion of the microporous passageway would be defined by the microbial adsorbent 22. Alternatively, in other embodiments, the fibers 14 will have an outer surface which defines a concavity. In these embodiments the portion of the outer surface which defines the concavity is, itself, defined by the microbial adsorbent.

In some embodiments, it may be desirable to form a laminate of the fabric 10 of the present invention and one or more other materials. Such a laminate would have the combined attributes of all of the individual layers. For example, the laminate could have a cloth-like appearance and feel, be breathable like cloth and still be able to prevent the passage of microbes therethrough. Of course, the term laminate is envisioned to include embodiments having two, three or more separate and discrete layers conventionally joined together by conventional lamination procedures.

It is to be understood that variations and modifications of the present invention may be made without departing from the scope of the invention. It is also to be understood that the scope of the present invention is not to be interpreted as limited to the specific embodiments disclosed herein, but only in accordance with the appended claims when read in light of the foregoing disclosure.

What is claimed is:

1. A breathable, microporous fabric defining a first surface and a second surface and comprising:
   a plurality of fibers which define at least one microporous passageway having a portion along its length equal to or less than 50 microns in diameter, the passageway allowing communication, through the fabric, between the first and second surfaces;
   a swellable material which is adapted, in the presence of a generally aqueous liquid, to increase its volume at least 2 times in no more than 1 second wherein a part of the microporous passageway is defined by the swellable material; and
   microbial adsorbent particles attached to the swellable material wherein a part of the microporous passageway is defined by at least one microbial adsorbent particle.

2. The fabric according to claim 1, wherein the fabric is formed from at least one material selected from the group consisting of polyolefins, polyamides, polyesters and copolymers and blends in any combination of these.

3. The fabric according to claim 2, wherein the polyolefin is selected from the group consisting of polypropylenes, polyethylenes, polybutylenes and copolymers and blends thereof.

4. The fabric according to claim 3, wherein the polyethylene is linear low density polyethylene.

5. The fabric according to claim 1, wherein the microbial adsorbent is adapted to adsorb at least one type of virus.

6. The fabric according to claim 1, wherein the microbial adsorbent is adapted to adsorb at least one type of bacteria.

7. The fabric according to claim 1, wherein the microbial adsorbent is adapted to adsorb at least one type of cyst.

8. The fabric according to claim 1, wherein the microbial adsorbent is adapted to adsorb at least one type of nematode.

9. The fabric according to claim 1, wherein the microbial adsorbent is a heavy metal.

10. The fabric according to claim 9, wherein the heavy metal is silver.

11. The fabric according to claim 1, wherein the microbial adsorbent is a metallic salt.

12. The fabric according to claim 11, wherein the metallic salt is a water-insoluble polyvalent metal salt.

13. The fabric according to claim 12, wherein the water-insoluble polyvalent metal salt is a salt of a metal selected from the group consisting of Group IB, Group IIA, Group IIB, Group IIIA, Group IVb, Group VIB metals.

14. The fabric according to claim 13, wherein the metal is selected from the group consisting of at least one of iron, aluminum, lead, magnesium, silver and calcium.

15. The fabric according to claim 12, wherein the salt is selected from the group consisting of hydroxides, phosphates, chromates, oxides and peroxides.

16. The fabric according to claim 15, wherein the salt is selected from the group consisting of one or more of ferric hydroxides, ferrous hydroxides, aluminum hydroxides, magnesium hydroxide, magnesium oxide, magnesium peroxide, lead chromate and calcium hydroxide.

17. The fabric according to claim 1, wherein the microbial adsorbent is selected from the group consisting of colloidal clays.

18. The fabric according to claim 17, wherein the colloidal clay is selected from the group consisting of bentonite and hectorite.

19. The fabric according to claim 18, wherein the bentonite is sodium bentonite.

20. The fabric according to claim 18, wherein the bentonite is calcium bentonite.

21. The fabric according to claim 1, wherein the fabric is a nonwoven fabric.

22. The fabric according to claim 1, wherein the fabric is a woven fabric.

23. The fabric according to claim 21, wherein the nonwoven fabric is a spunbonded fabric.

24. The fabric according to claim 21, wherein the nonwoven fabric is a meltblown fabric.

25. An item comprising the fabric according to claim 1.

26. The item according to claim 25, wherein the item is a garment.

27. The garment according to claim 26, wherein the garment is suitable for clean room attire.

28. The garment according to claim 27, wherein the garment is selected from the group consisting of a surgical gown, foot protectors, face masks, head or hair coverings, aprons, jackets, pants, gloves and coveralls.

29. The item according to claim 25, wherein the item is a sterile wrap.

30. The item according to claim 25, wherein the item is a surgical drape.

* * * * *